US010722427B2

(12) United States Patent
Cantor

(10) Patent No.: US 10,722,427 B2
(45) Date of Patent: Jul. 28, 2020

(54) HERMETICALLY SEALABLE CASE FOR MEDICAL DEVICE AND MEDICINE

(71) Applicant: Simon Charles Cantor, Paradise Valley, AZ (US)

(72) Inventor: Simon Charles Cantor, Paradise Valley, AZ (US)

( * ) Notice: Subject to any disclaimer, the term of this patent is extended or adjusted under 35 U.S.C. 154(b) by 90 days.

(21) Appl. No.: 15/939,666

(22) Filed: Mar. 29, 2018

(65) Prior Publication Data

US 2018/0214343 A1    Aug. 2, 2018

(51) Int. Cl.
| | |
|---|---|
| *A61J 1/16* | (2006.01) |
| *A61J 1/03* | (2006.01) |
| *F25B 21/04* | (2006.01) |
| *A61M 5/00* | (2006.01) |
| *G16H 40/63* | (2018.01) |
| *G16H 20/13* | (2018.01) |
| *G08B 25/01* | (2006.01) |

(52) U.S. Cl.
CPC ............... *A61J 1/165* (2013.01); *A61J 1/03* (2013.01); *A61M 5/002* (2013.01); *G16H 20/13* (2018.01); *G16H 40/63* (2018.01); *A61J 2200/40* (2013.01); *A61J 2200/42* (2013.01); *A61J 2200/44* (2013.01); *A61J 2200/50* (2013.01); *A61J 2200/72* (2013.01); *A61M 2205/3368* (2013.01); *A61M 2205/3372* (2013.01); *A61M 2205/3553* (2013.01); *A61M 2205/3592* (2013.01); *A61M 2205/36* (2013.01); *A61M 2205/3606* (2013.01); *A61M 2205/3633* (2013.01); *A61M 2205/3673* (2013.01); *A61M 2205/50* (2013.01); *A61M 2205/8206* (2013.01); *F25B 21/04* (2013.01); *G08B 25/016* (2013.01)

(58) Field of Classification Search
CPC ...... A61J 1/14; A61J 1/16; A61J 1/165; A61J 2200/40; A61J 2200/42; A61J 2200/44; A61J 2200/50; A61J 2200/72; F25B 21/04; B65D 81/02; B65D 81/26; B65D 83/10
USPC ........ 206/438, 364, 365; 220/592.01–592.28
See application file for complete search history.

(56) References Cited

U.S. PATENT DOCUMENTS

| 1,485,665 | A | * | 3/1924 | Botner ..................... A23G 9/08 220/592.14 |
| 3,034,845 | A | | 5/1962 | Naumann |
| 3,910,441 | A | | 10/1975 | Brmming |
| 3,961,720 | A | | 6/1976 | Potter, Jr. |
| 4,119,248 | A | | 10/1978 | Butler et al. |

(Continued)

*Primary Examiner* — Jianying C Atkisson
*Assistant Examiner* — Miguel A Diaz
(74) *Attorney, Agent, or Firm* — Henricks Slavin LLP

(57) ABSTRACT

A case includes a pocket for hermitically storing medical device(s) and medicine. The case may include a manual or motorized pump that can generate vacuum pressure within the pocket to thermally insulate the pocket from the atmosphere to minimize temperature fluctuations within the pocket. The case may also include a cooling and/or heating system to control the temperature within the pocket within a desired range to prolonging the potency and the life expectancy of the drug, such as epinephrine, stored within the pocket. The case may also be equip with a communication device that can link with user's mobile device so that in case of an emergency, the communication device can alert the mobile device, which can then notify emergency personal for assistance.

7 Claims, 10 Drawing Sheets

(56) References Cited

U.S. PATENT DOCUMENTS

| | | | | |
|---|---|---|---|---|
| 4,249,583 A * | 2/1981 | Lundbladh | | B65B 31/047 |
| | | | | 116/268 |
| 4,250,998 A * | 2/1981 | Taylor | | A45C 11/20 |
| | | | | 206/570 |
| 4,278,114 A * | 7/1981 | Ruberg | | A23L 3/0155 |
| | | | | 137/565.25 |
| 4,573,581 A * | 3/1986 | Galloway | | A61J 1/165 |
| | | | | 206/37 |
| 4,975,028 A * | 12/1990 | Schultz | | A23L 3/0155 |
| | | | | 137/843 |
| 5,189,890 A * | 3/1993 | Kitayama | | F25D 3/107 |
| | | | | 62/293 |
| 5,390,809 A * | 2/1995 | Lin | | B65B 31/047 |
| | | | | 137/522 |
| 5,419,435 A * | 5/1995 | Perzan | | B65F 1/141 |
| | | | | 206/366 |
| 5,469,979 A * | 11/1995 | Chiou | | B65B 31/047 |
| | | | | 141/65 |
| 5,483,799 A * | 1/1996 | Dalto | | A61J 1/165 |
| | | | | 62/3.6 |
| 5,558,243 A * | 9/1996 | Chu | | B65D 81/2038 |
| | | | | 215/228 |
| 5,566,828 A * | 10/1996 | Claes | | A61M 5/003 |
| | | | | 206/1.5 |
| 5,611,376 A * | 3/1997 | Chuang | | B65B 31/047 |
| | | | | 141/65 |
| 5,692,632 A * | 12/1997 | Hsieh | | B65D 81/20 |
| | | | | 215/228 |
| 6,003,666 A | 12/1999 | Dougherty | | |
| 6,104,611 A | 8/2000 | Glover et al. | | |
| 6,644,489 B2 * | 11/2003 | Chang | | B65D 81/2038 |
| | | | | 215/260 |
| 6,652,251 B1 * | 11/2003 | Chen | | F04B 35/04 |
| | | | | 141/65 |
| 6,968,888 B2 | 11/2005 | Kolowich | | |
| 7,041,123 B2 | 5/2006 | Stapf et al. | | |
| 7,048,136 B2 * | 5/2006 | Havens | | B65D 51/1644 |
| | | | | 206/524.8 |
| 7,315,246 B2 * | 1/2008 | Rajapakse | | B65D 90/22 |
| | | | | 340/545.1 |
| 8,205,468 B2 | 6/2012 | Hemminger et al. | | |
| 8,226,610 B2 * | 7/2012 | Edwards | | A61M 5/19 |
| | | | | 604/137 |
| 9,096,365 B2 * | 8/2015 | Kim | | B65D 81/2038 |
| 9,151,531 B2 | 10/2015 | Wengreen et al. | | |
| 9,381,294 B2 | 7/2016 | Ziegner | | |
| 9,668,510 B2 * | 6/2017 | Doman | | A23L 3/0155 |
| 9,707,156 B2 * | 7/2017 | Wengreen | | B65D 81/383 |
| 10,143,979 B2 * | 12/2018 | Vogt | | A61B 17/8833 |
| 10,517,662 B2 * | 12/2019 | Vogt | | B01F 13/003 |
| 10,551,407 B2 * | 2/2020 | Chennakeshu | | G01P 15/14 |
| 2006/0081599 A1 * | 4/2006 | Anderson | | A47J 36/2433 |
| | | | | 219/438 |
| 2006/0191282 A1 | 8/2006 | Sekiya et al. | | |
| 2007/0210090 A1 | 9/2007 | Sixt et al. | | |
| 2009/0049845 A1 * | 2/2009 | McStravick | | F25B 21/02 |
| | | | | 62/3.62 |
| 2009/0145793 A1 * | 6/2009 | Hyde | | A61J 1/165 |
| | | | | 206/438 |
| 2009/0179053 A1 | 7/2009 | Cooney et al. | | |
| 2010/0329074 A1 * | 12/2010 | Vogt | | B01F 15/0201 |
| | | | | 366/190 |
| 2012/0026825 A1 * | 2/2012 | Vogt | | A61B 17/8833 |
| | | | | 366/176.3 |
| 2012/0132675 A1 * | 5/2012 | Vogt | | A61B 17/8825 |
| | | | | 222/327 |
| 2014/0144799 A1 * | 5/2014 | Praedel | | A61L 2/26 |
| | | | | 206/438 |
| 2014/0252927 A1 | 9/2014 | Denney et al. | | |
| 2014/0367288 A1 | 12/2014 | Ziegner | | |
| 2015/0027157 A1 * | 1/2015 | Chou | | F25D 17/042 |
| | | | | 62/271 |
| 2015/0151893 A1 | 6/2015 | Wergreen et al. | | |
| 2015/0249478 A1 | 9/2015 | Greiner | | |
| 2016/0015910 A1 * | 1/2016 | Mukai | | A61M 5/002 |
| | | | | 206/365 |
| 2016/0159632 A1 * | 6/2016 | Wheatley | | G06F 19/3475 |
| | | | | 222/1 |
| 2016/0193408 A1 | 7/2016 | Schweikert et al. | | |
| 2016/0242598 A1 * | 8/2016 | Alexander | | A47J 36/2433 |
| 2016/0243000 A1 * | 8/2016 | Gray | | F25B 21/02 |
| 2017/0014786 A1 * | 1/2017 | Vogt | | B01F 15/0258 |
| 2017/0023290 A1 * | 1/2017 | Demuth | | F25D 11/003 |
| 2017/0094395 A1 * | 3/2017 | McPeak | | B65D 43/16 |
| 2017/0155419 A1 | 6/2017 | Greiner | | |
| 2017/0312119 A1 | 11/2017 | Oh | | |
| 2017/0340403 A1 | 11/2017 | Roberts-Monteleone | | |
| 2017/0361028 A1 | 12/2017 | Friedman | | |
| 2018/0008788 A1 * | 1/2018 | Kamen | | A61M 5/14244 |
| 2018/0036202 A1 | 2/2018 | Wengreen et al. | | |
| 2018/0172722 A1 * | 6/2018 | He | | G01C 21/10 |
| 2018/0194533 A1 * | 7/2018 | Bramwell | | B65D 81/3813 |
| 2018/0214343 A1 * | 8/2018 | Cantor | | A61J 1/165 |
| 2019/0277553 A1 * | 9/2019 | Vlahinos | | F25D 17/045 |
| 2019/0357709 A1 * | 11/2019 | Klemm | | A47G 19/2288 |
| 2019/0390890 A1 * | 12/2019 | Alexander | | F25D 11/003 |
| 2020/0029714 A1 * | 1/2020 | Nguyen | | C02F 1/325 |

* cited by examiner

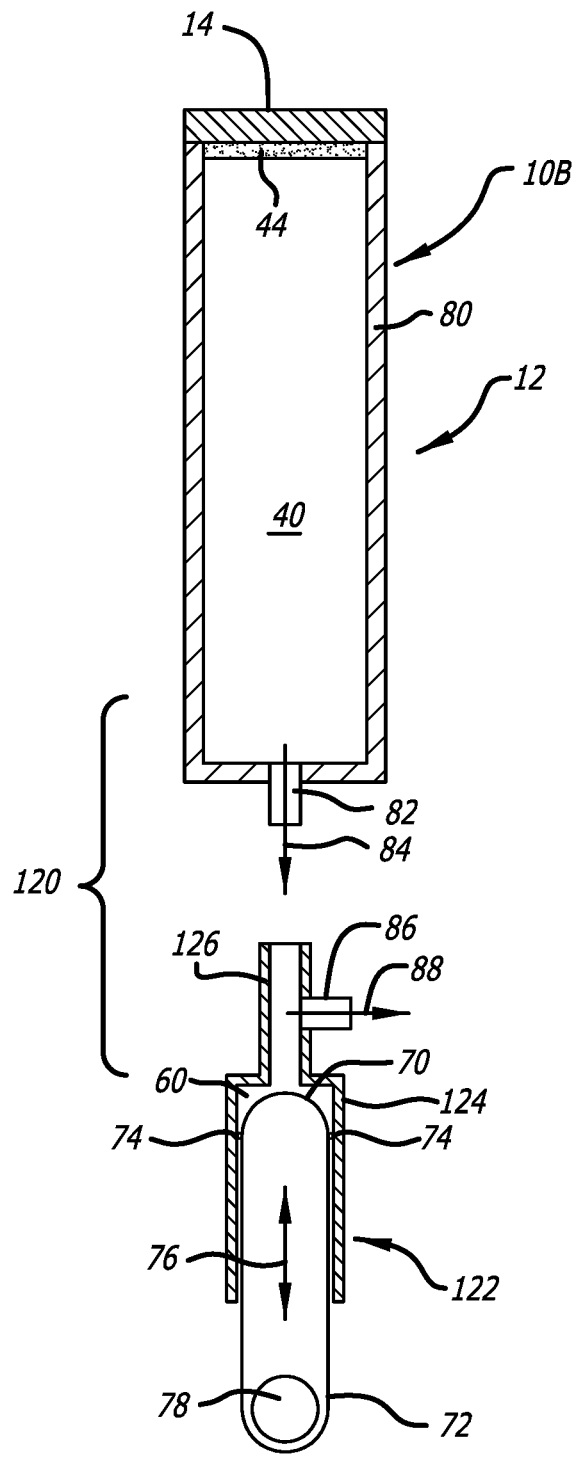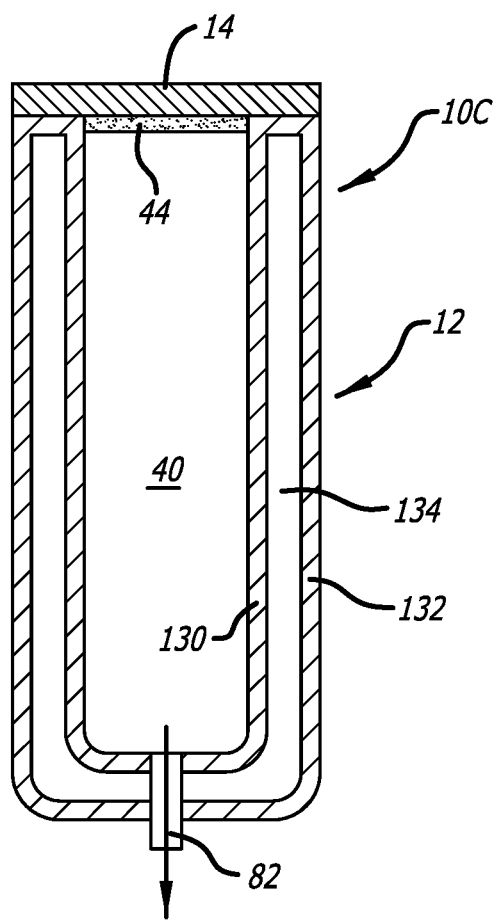
FIG. 6
FIG. 7

HERMETICALLY SEALABLE CASE FOR MEDICAL DEVICE AND MEDICINE

BACKGROUND OF THE INVENTION

1. Field of the Invention

A portable case provides one or more pockets to hold a medical device such as an auto-injectable device that can be self-administered to deliver the drug epinephrine in response to an allergic reaction and a tablet of diphenhydramine such as Benadryl®; and in particular, the pocket may be hermetically sealable to isolate the medical device and medicine from extreme temperature fluctuations.

2. Background of the Invention

People with anaphylaxis condition can have allergic reactions to certain type of food and venom such as nuts and bees, respectively, where in some cases allergies can unexpectedly trigger a severe allergic reaction requiring an immediate medical attention. In the United States, it is estimated that six to ten percent of children now have some form of food allergies, some of which can lead to life-threatening allergic reactions. For an immediate treatment, the medical community recommends that the patients who are at high risk to severe allergic reactions carry an auto-injectable device that can be self-administered to deliver the drug epinephrine, also known as adrenaline, which is a life-saving medication that acts on the whole body to shut down the allergic response at least temporarily so that the patient can seek professional medical attention. This means that people with anaphylaxis may need to carry with them an injectable device when they travel away from home such as to office, school, restaurants and etc.

There are several auto-injectable devices available in the market today such as those marketed under the brand names of EPIPEN® and AUVI-Q® (collectively referred to as "Injector Device(s)"). These Injector Devices are popular because they are portable and they contain a calibrated dose of epinephrine that can be self-administered safely when needed via intramuscular injection to quickly shut down the allergic response.

The severity of the allergic reaction can vary depending on the cause and the environmental factors. That is, while some allergic reactions may require an immediate medical treatment, most reactions may be treatable with the over the counter medicine such as diphenhydramine, which is better known as Benadryl®. Accordingly, many people with anaphylaxis carry with them Benadryl to treat a milder reaction, and an Injector Device to treat more severe reaction. This also means that people with anaphylaxis need to remind themselves to carry both items with them at all times just in case of an allergic reaction, or have ready access to such medical devices where they live and/or frequently visit such as school and office. However, carrying both items separately is not always easy to remember nor convenient because an Injector Device is rather bulky compared to Benadryl, and the tablet can easily break apart. Moreover, these medical devices can be expensive for many users so having multiple medical devices stored in different locations in case of an emergency allergic reaction can be an expensive proposition. For instance, as of 2018, retail price of two packs of EPIPEN® is about US$300.00, and having to purchase multiple devices for different locations can be an expansive proposition. Accordingly, there is a need for a more convenient way of carrying both an Injector Device and a tablet of Benadryl at all times.

Another problem with Injector Devices such as EPIPEN® and AUVI-Q® is that the environment can impact the lifespan and the potency of the drug epinephrine contained therein. For instance, manufactures of these Injector Devices recommend the users to store the Injector Devices in areas where the temperature fluctuates between 59°-86° F. (15°-30° C.), but a narrower temperature range of 68°-77° F. (20°-25° C.) is suggested as the preferred temperature range to maintain the effectiveness of epinephrine. In fact, the manufactures of these Injector Devices explicitly instruct the users to not expose the Injector Devices to extreme heat or cold, not to store them in refrigerator or freeze them, not to store the Injector Devices in the vehicle's glove box, and even protect the Injector Device from light. In other words, the Injector Devices need to be kept at the narrow temperature range in order to not compromise the potency of the drug epinephrine contained within the Injector Devices. Such instructions, however, may be difficult to follow especially if the user lives in a warm climate such as Phoenix, Ariz. where the temperature can reach well over 100° F. for many months of the year or if the user lives in a cold climate where the temperature can be well below 50° F. for many months. For instance, it is estimated that the average annual temperature of 37 states in the U.S.A is below 59° F. (15° C.), which would mean that in most states Injector Devices can be subjected to temperatures below even the broader temperature range of 59°-86° F. permitted by the manufactures.

Yet another problem with the Injector Devices is that when a user is having a severe allergic reaction, it can be frightening, especially for a child, as the reaction can lead to trouble with breathing as the throat closes, which may lead to the heart beating faster and then to nausea, abdominal pain, and/or vomiting. The suddenness of the intense pain and the involuntary bodily functions can hinder the user from thinking properly temporarily and impairing the user from self-administering the Injector Device, and then remembering to call for an emergency assistance.

Some ideas have been proposed to address the above-mentioned problems with the Injector Devices. For instance, US Patent Publication No. 2014/0367288, entitled AUTO-INJECTOR CASE ("the '367288 Publication"), published Dec. 18, 2014, which is hereby incorporated by reference in its entirety, is directed providing a case to hold one or more injector devices with a temperature sensor to record the temperature within the case so that the user can be informed if the injector device has been heated to a degree that reduces the effectiveness of the epinephrine therein but the case does not warn the user that the drug in the injector device is being compromised due to exposure to extreme temperatures. The '367288 Publication also discloses utilizing a foam insulation around the casing to minimize temperature variation within the casing. The '367288 Publication, however, still does not address the problem of the Injector Devices being exposed to the temperatures below and above the recommended temperature range of 59°-86° F., which can often occur, thereby reducing the effectiveness of epinephrine even before its proscribed expiration date. Moreover, the surrounding foam insulation material can increase the size of the case, thereby making the case bulky and inconvenient to carry. Accordingly, the manufactures of EPIPEN® and AUVI-Q® instruct the user to periodically inspect the epinephrine solution through the viewing window on the Injector Device to ensure that the solution is clear, which may indicate that the epinephrine is still effective. If the solution, however, is discolored or cloudy or if the solution contains solid particles, then the manufactures instructs the user to replace the Injector Device even if it is before the expiration date, which is about 18 months post its manufactured date. However, the expiration date includes the time it takes to distribute and reach the user's hands so that the actual allotted time before the expiration date is about one year.

While users should heed manufactures' warnings and follow their instructions, in practice, such instructions put many users in a compromising position because the price of Injector Devices, such as EPIPEN®, have risen substantially recent years as it has been well publicized and scrutinized. This means that for some users who are less fortunate, they may not be able to afford to replace the Injector Device even though the epinephrine may not be as effective as it should be due to the exposure to hot and cold temperatures—especially if this happens before the expiration date. Accordingly, there is a need to keep the Injector Devices within the recommended room temperature range to maintain the effectiveness of the epinephrine as long as possible.

Another idea that has been proposed is disclosed in US Patent Publication No. 2017/0361028, entitled INJECTOR DEVICE ("the '361028 Publication"), published Dec. 21, 2017, which is hereby incorporated by reference in its entirety, directed to a mobile phone case that can hold a mobile phone and an injector device behind the phone inside an all-in-one case. The integrated injector device is part of the phone case with a trigger, spring-loaded needle and reservoir holding a medication such as epinephrine or insulin. The mobile phone case can also communicate injection data to the phone to communicate the injection data to an emergency service provider. One of the problems with a phone case that integrates the injector device next to the mobile phone is that the injectable device is close the battery of the mobile phone, which can radiate heat. This is especially true when the phone is being charged throughout the day and/or use a lot of data such as when downloading an app, playing games and streaming video, which can cause the battery to heat up. In such circumstances, the temperature of the phone can exceed well over 100° F. or over the recommended temperature of storing the injectable device, which can degrade the effectiveness of epinephrine as discussed above. Accordingly, there still is a need to maintain the Injector Devices within the recommended room temperature range without exposing the device to a heat source.

SUMMARY OF THE INVENTION

One of the aspects of the invention is to provide a case with one or more pockets for storing medical devices and medicine. The case may include a manual or motorized pump that can generate vacuum pressure within the pocket to thermally insulate the pocket from the atmosphere to minimize temperature fluctuations within the pocket. The case may also include a cooling and/or heating system to control the temperature within the pocket within a desired range to prolonging the potency and the life expectancy of the drug, such as epinephrine. This may allow the user to store the case within an area that is convenient to the user with a lesser concern about exposing the medicine to extreme temperature such as within a vehicle. The case may be store a variety of medical devices, drugs, and medicine, and especially for those who may have an urgent need for medicine such as people with anaphylaxis condition can have allergic reactions to certain type of food and venom such as from nuts and bees, respectively. The case may be equip with a communication device that can link with user's mobile device so that in case of an emergency, the communication device can alert the mobile device, which can then notify emergency personal for assistance.

In this this regard, one of the aspects of the invention is directed to a case for storing medical device, the case comprising: a housing having an outer sidewall with an inner wall dividing a pocket and a chamber, the pocket adapted to receive a medical device; a cover adapted to open and close to seal the pocket; a first one-way valve coupled to the inner wall to allow air to pass from the pocket to the chamber; and a plunger adapted to move within the chamber between an retracted position and an extended position such that as the plunger moves from the retracted position to the extended position air within the pocket flows through the first one-way valve and into the chamber to generate a vacuum pressure within the pocket that is lower than the atmospheric pressure. Moreover, the case may further include a thermoelectric cooler (TEC) juxtaposed to the pocket such that powering the TEC can either cool or heat the pocket. In addition, the case may include a temperature sensor that monitors the temperature within the pocket and a processor that controls the power provided to the TEC to cool the pocket if the measured temperature is above the desired temperature range and heat the pocket if the measured temperature is below the desired temperature range. The case can also include first and second detection sensors and a communication device, the first detection sensor coupled to the cover and the second detection sensor coupled to the housing such that when the cover is closed relative to the housing, the first and second detection sensors are closed and when the cover is open relative to the housing, the first and second detection sensors are open, the communication device communicably coupled to the processor and capable of wirelessly communicating with a mobile phone such that when the first and second detection sensors detect that the cover is open relative to the housing, the processor send a message to the mobile phone that the cover is open.

Another aspect of the invention is directed to a case system for storing medicine, the case system comprising: a housing having: a pocket adapted to receive a medicine, a passage opening to allow atmospheric air to enter the pocket, an one-way valve to allow air to pass from the pocket to atmosphere but not enter the pocket, an actuator moveably couple to the housing, and a handle having a first end and a second end, the first end of the handle pivotably coupled to the actuator and the handle is coupled to the housing via a link such that when the handle is in a retracted position the handle plugs the passage opening, and when the handle moves from the retracted position to an extended position the handle unplugs the passage opening; and a cover adapted to move between an open position and a close position to seal the pocket such that when the cover is in the close position and the handle is in the retracted position the actuator is underneath the cover with a gap therebetween, and as the handle moves from the retracted position to the extended position the handle unplugs the passage opening first and then the actuator moves the cover from the closed position to the open position. Moreover, the case system may further include a pump having a barrel with a chamber adapted to receive a plunger, a protruding member adapted to releasably couple to the one-way valve, and a second one-way valve coupled to the protruding member to allow air to pass from the chamber to atmosphere such that as the plunger moves from a retracted position to an extended position relative to the chamber the air within the pocket flows through the one-way valve and into the chamber to generate a vacuum pressure within the pocket that is lower than the atmospheric pressure. The case system may also a mobile communication device that can be activated by an emergency button provided with the case. In case of an emergency, the button may be activated the user to cause the mobile communication device to transmit a message, via the mobile network, to a predetermined emergency contact personals such as next to kin, doctors, and emergency responders.

Yet another aspect of the invention includes a method of requesting an emergency assistance, the method comprising: receiving a request from a request mobile device for an emergency assistance with the location of the mobile device and the nature of the emergency; identifying registered users within a network with mobile devices and medicine within a predetermined range of the request mobile device that can assist the user of the request mobile device based on the nature of the emergency; sending an emergency assistance request to the mobile devices of the users that can assist the user of the request mobile device; receiving confirmation from respondent users who have accepted the emergency assistance request; selecting at least one of the respondent users who can best respond to the request mobile device; sending a confirmation message to the at least one of the respondent users selected from the selecting step to assist the user of the request mobile device; and sending a cancellation notice to all other respondent users.

Still another aspect of the invention includes a method of insulating a medicine, the method comprising: receiving a medicine within a pocket; sealing the pocket from atmosphere; removing at least a portion of the air within the pocket; and powering a TEC to cool the pocket if temperature within the pocket rises above a desired upper temperature.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 6 shows a cross-sectional view of a sealable case system.

FIG. 7 shows a cross-sectional view of another embodiment of a case.

DETAILED DESCRIPTION OF THE INVENTION

Figure 1:
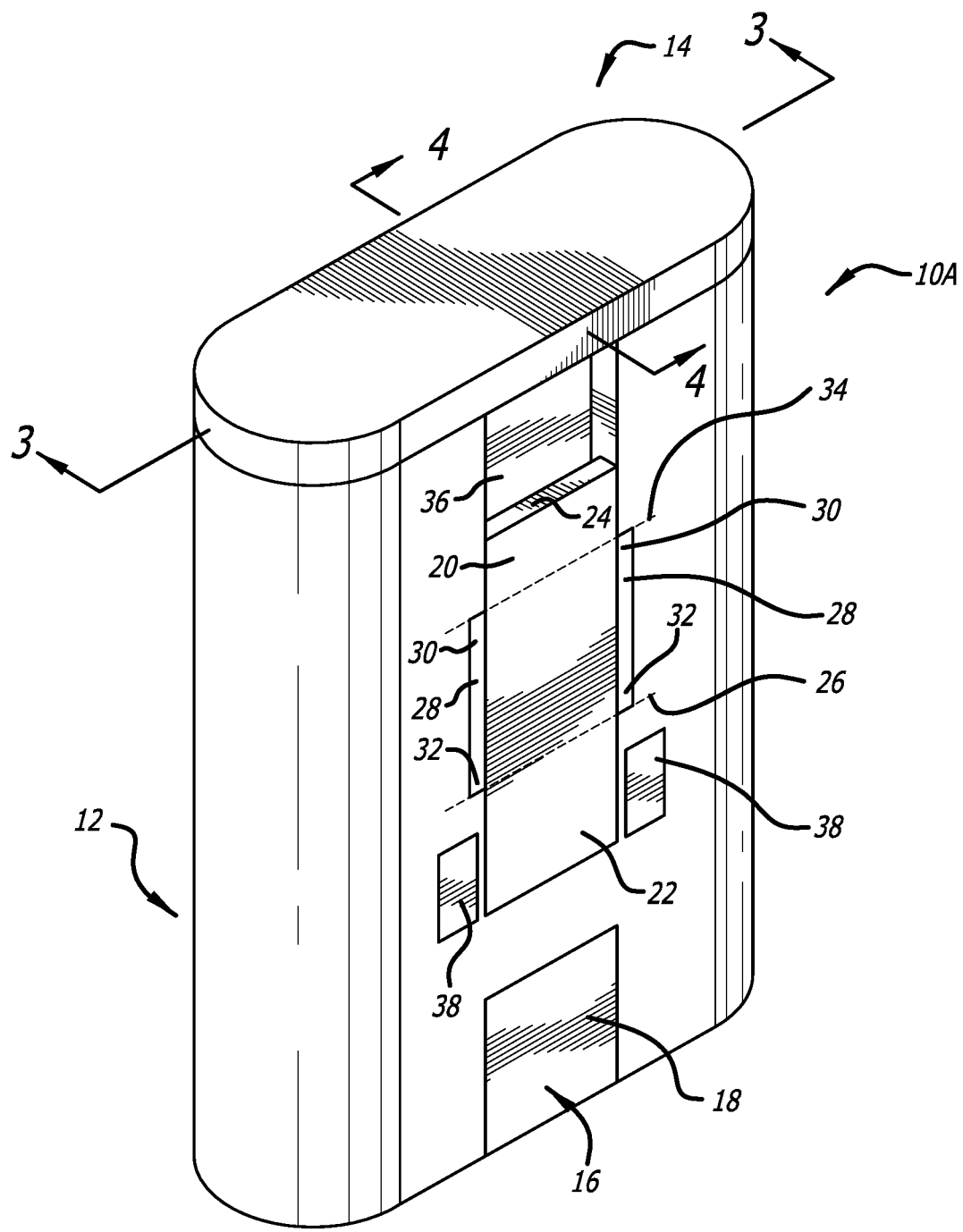
FIG. 1 shows a perspective view of a case configured to hold one or more medical devices and/or medicine.

The various aspects of the invention can be better understood with reference to the drawings and description described below. The components in the figures, however, are not necessarily to scale, emphasis instead being placed upon illustrating the principles of the various aspects of the invention. In general, when the terms "may", "is", and "are" are used as a verb in the description corresponding to a particular subject matter, these terms are generally used in this disclosure as an expression of a possibility of such subject matter rather than as a limiting sense such as when the terms "shall" and "must" are used. For example, when the description states that the subject matter "may be" or "is" circular, this is one of many possibilities, such that the subject matter can also include an oval, square, regular, irregular, and any other shapes known to a person of ordinarily skilled in the art rather than being limited to the "circular" shape as described and/or illustrated in the corresponding referenced figure. In addition, when the term "may", "is", and "are" are used describe a relationship and/or an action, these terms are generally used in this disclosure as an expression of a possibility. For example, when the description states that a subject matter A "may be" or "is" adjacent to a subject matter B, this can be one of many possibilities including the possibility that the subject matter A is not adjacent to the subject matter B as it would be understood by a person of ordinarily skilled in the art.

Moreover, it is within the scope of the invention to combine the various embodiments disclosed relating to one or more particular drawing and their corresponding descriptions with one or more of other drawings and their corresponding descriptions when such combination is achievable by one of ordinary skilled in the art. The same referenced numerals referred to in the drawings and description generally correspond to same or similar parts throughout the disclosure.

Figure 5:
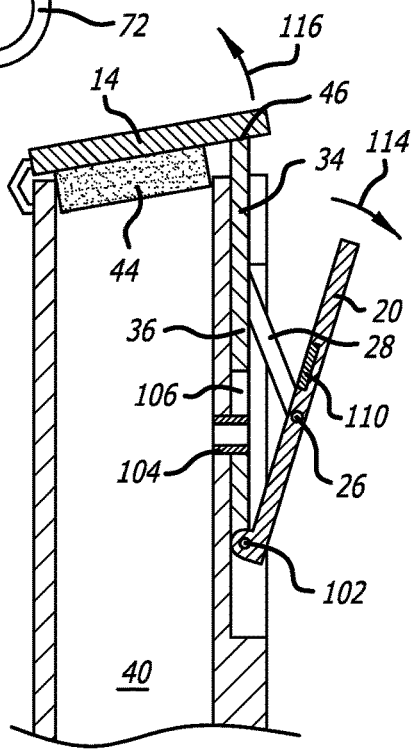
FIG. 5 shows a partial cross-sectional view along the sectional-line 4-4 shown in FIG. 1 with the handle in the extended position.

FIG. 1 shows a perspective view of a case 10A configured to hold one or more medical devices and/or medicine. The case 10A includes a housing 12 and a cover 14 configured to enclose the housing 12. The housing 12 may include a pocket 16 with a door 18 that may open and close as discussed in more detail below. The housing 12 may also include a handle 20 having a first end 22 and a second end 24 with a third pivotal axis 26 therebetween the two ends 22 and 24. The housing 12 may also include one or more links 28 having a proximal end 30 and a distal end 32. The proximal end 30 of the link 28 may be pivotably coupled to the housing 12 about a pivot axis 34, and the distal end 32 of the link 28 may be pivotably coupled to the handle 20 about the pivot axis 26. As discussed in more detail below, the first end 22 of the handle 20 may be pivotably coupled to an actuator 36 such that as the handle 20 is moved from a retracted position as shown in FIG. 1 to an extended position as shown in FIG. 5 below, the actuator 36 may move from a retracted position to an extended position as well, and vice versa, relative to the housing to assist in opening the cover 14 from the housing 12. The housing 12 may also include one or more windows 38 to allow a user to inspect the medical device(s) and medicines held within the case 10.

Figure 2:
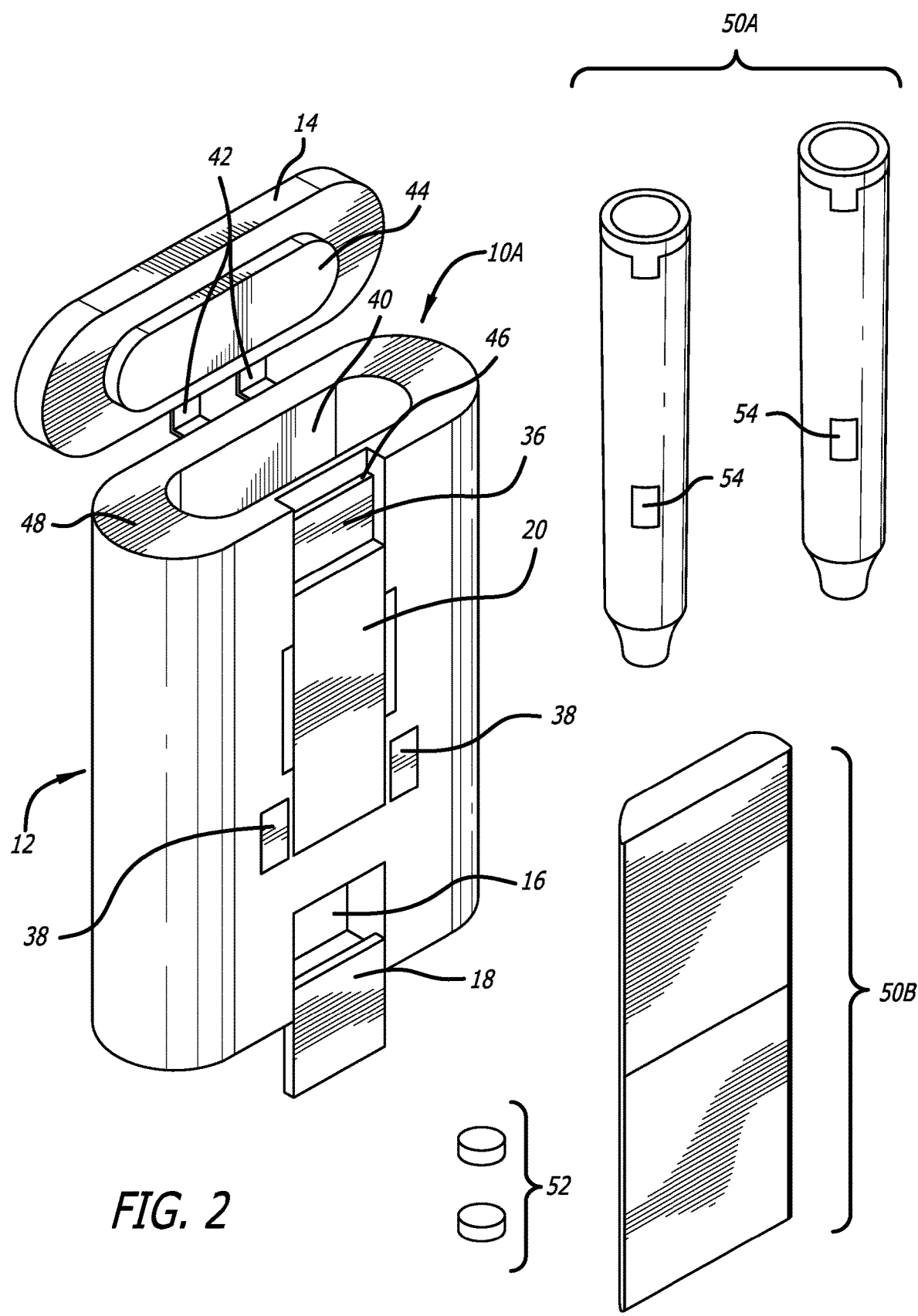
FIG. 2 shows the case with the cover in an open position.

FIG. 2 shows the case 10A with the cover 14 in an open position that shows the housing 12 having a pocket 40 adapted to receive one or more medical devices and/or medicines. The cover 14 may be attached to the housing 12 via flexible brackets 42 or through a variety of mechanisms known to one skilled in the art. The underside of the cover 14 may have a cap 44 configured to seal the pocket 40 once the cover 14 is in a closed position relative to the housing 12. The cap 44 may be formed from a gasket like material to seal the pocket once the cap 44 is inserted into the pocket 40. Note that with the cover 14 in the open position, the tip 46 of the actuator 36 may be shown to be not flush with the top side 48 of the housing 12 to allow the handle 20 to be pulled more readily, as discussed in more detail below.

The pocket 40 may be configured to hold one or more medical devices such as injector devices 50A and 50B and medicine 52. In particular, the medical devices 50A may general represent the outer shape and size of EPIPEN®, the medical devices 50B may general represent the outer shape and size of AUVI-Q®, and the medicines 52 may general represent the tablet form of BENADRYL®. Note that the medical device and/or medicine which may be stored in the pocket 40 may be any device and/or medicine that may be sensitive to temperature fluctuation such as insulin for diabetes and nitroglycerin for heart disease. Moreover, the pocket 40 may be sized to have enough room to hold one or more medical devices 50A side by side and medicine 52 or the medical devices 50B arranged one on top of the other and medicine 52. Alternatively, the door 18 may slide open to expose the pocket 16 which is adapted to receive one or more medicines 52 for easy access by the user in case of an allergic reaction. Accordingly, the pocket 40 may be sized to hold more than one type of medical devices and medicine. In addition, some medical devices 50A may have a window 54 to allow the user to inspect the drug epinephrine contain therein to ensure that the epinephrine is still clear which may be indicative that the drug is still potent and effective. The pocket 40 may be configured so that the medical devices 50A may be held within the pocket 40 so that the window 54 may be aligned with the window 38 of the housing 12 to allow the user to inspect the drug in the medical devices 50A held within the pocket 40 without having to open the cover 14 and remove the medical device 50A to inspect the medical device.

Figure 3:
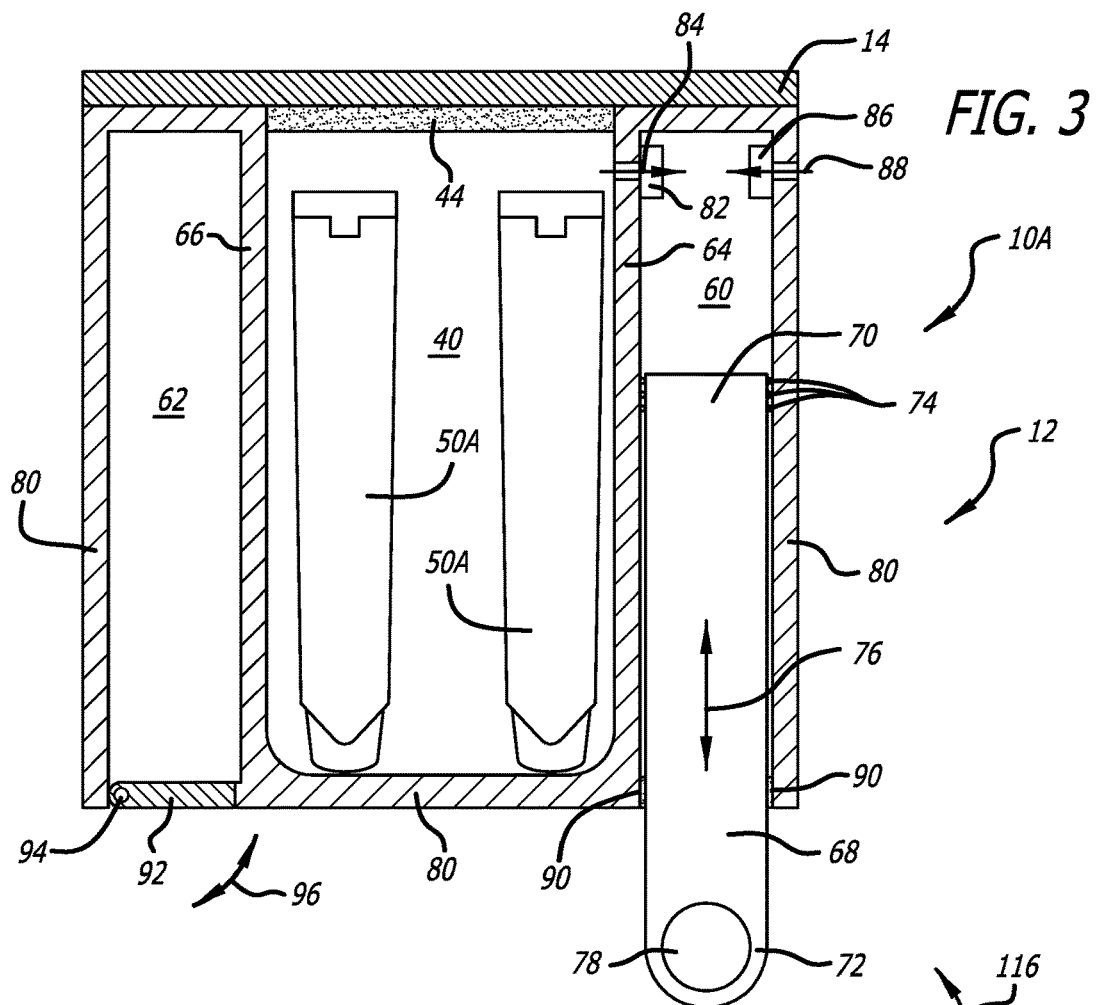
FIG. 3 shows a cross-sectional view of the case along the sectional-line 3-3 shown in FIG. 1.

FIG. 3 shows a cross-sectional view of the case 10A along the sectional-line 3-3 shown in FIG. 1 illustrating the cover 14 with the cap 44 enclosing the pocket 40 formed within the housing 12. As discussed above in reference to FIG. 2, the pocket 40 may be sized to hold one or more medical devices 50A or 50B such that once of the cap 44 encloses the pocket 40, the items stored within the pocket 40 may be hermetically sealed in a manner described below. The housing 12 may be divided into several sections such that the pocket 40 may be formed between a first chamber 60 and a second chamber 62 defined by a first inner wall 64 separating the pocket 40 from the first chamber 60, and a second wall 66 separating the pocket 40 from the second chamber 62 with the outer sidewalls 80 defining the pocket and the chambers. The first chamber 60 may be adapted to receive a plunger 68 having a first end 70 and a second end 72. The first end 70 of the plunger 68 may have one or more seals 74 to provide substantial air tightness between the plunger 68 and the first chamber 60 as the plunger 68 moves in and out of the first chamber 60 as indicated by the double ended direction arrows 76. The second end 72 of the plunger 68 may have an opening 78 to allow a user to grab onto the plunger 68 to move the plunger 68 in and out of the first chamber 60.

The housing 12 may have a first one-way valve 82 coupled to the first inner wall 64 to draw air out of the pocket 40 as indicated by the direction arrow 84 but not in the opposite direction or into the pocket 40. The sidewall 80 may have a second one-way valve 86 to draw air out of the first chamber 60 as indicated by the direction arrow 88 but not in the opposite direction or into the first chamber 60. Accordingly, once the cap 44 substantially seals the pocket 40, the air inside the pocket 40 may in effect only be removed via the first one-way valve 82 and no other means. As such, as the plunger 68 is withdrawn from the first chamber 60, the vacuum pressure is created therein since the atmospheric air cannot enter the first chamber 60 due to the second one-way valve 86 that prevents atmospheric air from entering the first chamber 60. The greater vacuum pressure (lower pressure) within the first chamber 60 relative the pressure within the pocket 40 causes the air within the pocket 40 to flow from the pocket 40 through the first one-way valve 82 and into the first chamber 60, thereby creating a vacuum pressure within the pocket 40. The housing 12 may have a block 90 near the opening of the first chamber 60 to engage with the seals 74 to stop the plunger 68 from fully withdrawing from the housing 12 once the plunger 68 has reached its extended position. To generate additional vacuum pressure within the pocket 40, the plunger 68 may be reinserted into the first chamber 60, which causes the air within the first chamber 60 to exit via the second one-way valve 86 but not via the first one-way valve 82 to maintain the vacuum pressure generated within the pocket 40 due to the first cycle of withdrawing the plunger 68 from the first chamber 60. As such, as the plunger 60 is cycled in and out of the first chamber 60, in the manner discussed above, the vacuum pressure within the pocket 40 may be increased to hermetically seal the medical devices and medicine stored within the pocket 40 to substantially isolate the items from the atmosphere. In addition, with the vacuum pressure generated, i.e.—less atoms, within the pocket 40, the temperature fluctuations within the pocket 40 may be minimized to keep the drug potent and effective for a longer period of time compared to the drug exposed to the atmosphere such as oxygen and extreme temperature fluctuations. Note that it is within the scope of the invention to utilize a variety of mechanisms and method for generating vacuum pressure within the pocket 40 such as through a motorized pump that may not require the one-way valve or valves.

The housing 12 may also have a door coupled to the housing 12 via a hinge 94 to allow the door 92 to open and close as indicated by the direction arrow 96. The door 92 allows access to the second chamber 62 to hold other items such as tablet medicines and other medical devices which may not be sensitive to atmosphere or temperature fluctuations.

Figure 4:
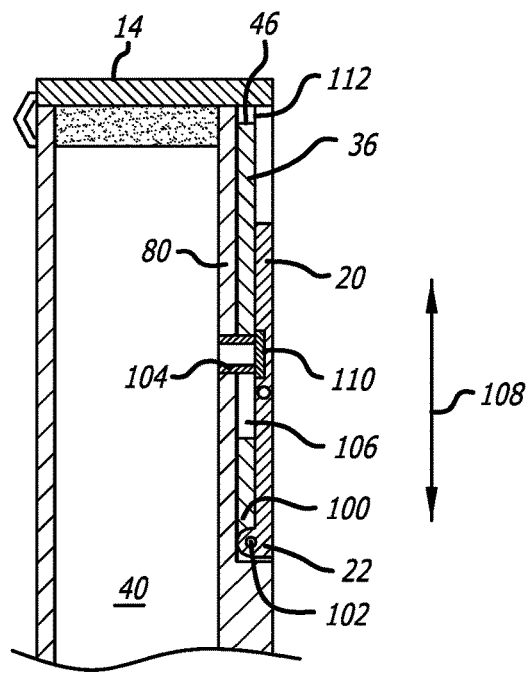
FIG. 4 shows a partial cross-sectional view along the sectional-line 4-4 shown in FIG. 1 with the handle in the retracted position.

FIG. 4 shows a partial cross-sectional view along the sectional-line 4-4 shown in FIG. 1 illustrating the handle 20 and the actuator 36 in a retracted position and the manner that the handle 20 may operate with the actuator 36. The actuator 36 may be located between the handle 20 and the sidewall 80 of the housing 12 to allow the actuator 36 to slide up and down relative to the sidewall 80 as indicated by the double ended direction arrows 108. The actuator may have a base end 100 pivotably coupled to the first end 22 of the handle 20 about a pivot axis 102. As discussed above in reference to FIG. 2, the tip 46 of the actuator 36 may not reach the cover 14 when the handle 20 is in a fully retracted position, as shown in FIG. 4. That is, there may be a gap 112 between the tip 46 and the cover 14 when the handle 20 is in a fully retracted position. The sidewall 80 defining the pocket 40 may have an air passage tube 104 protruding from the sidewall 80, and the actuator 36 may have an elongated slot opening 106 adapted to receive the tube 104. The slot opening 106 may be elongated along the longitudinal axis as indicated by the direction arrows 108 to allow the actuator 36 to slide up and down relative to the tube 104 and the sidewall 108. The handle 20 may have a plug 110 to cover the tube 104 when the handle is in a retracted position, as illustrated in FIG. 4, to form an air tight seal against the tube 104. Accordingly, when the handle 20 is in a retracted position, vacuum pressure may be generated within the pocket 40 in a manner described above in reference to FIG. 3.

FIG. 5 shows a partial cross-sectional view along the sectional-line 4-4 shown in FIG. 1 illustrating the handle 20 and the actuator 36 in an extended position and the manner in that the handle 20 may cause the actuator 36 to open the cover 14. As discussed above in reference to FIG. 1, the housing 12 may include the links 28 where the distal end 32 of the link may be pivotably coupled to the handle about the pivot axis 26, and the proximal end 30 may be pivotably coupled to the housing 12 about the pivot axis 34. As such, as the handle 20 moves from the retracted position, as shown in FIG. 4, to the extended position, as shown in FIG. 5, the plug 110 uncovers the tube 104, which exposes the pocket 40 to the atmosphere to allow the outside air to enter the pocket 40 to relieve the vacuum pressure within the pocket 40. That is, the vacuum pressure within the pocket 40 may resist the cap 44 and the cover 14 from opening. Accordingly, in order to assist the user from opening the cover 14, the vacuum pressure may be relieved prior to opening the cover—especially if the user is experiencing an allergic reaction at a time when it may be difficult to control his or her bodily functions such as its hands.

In reference to FIG. 5, in order to open the cover 14, the user may pull on the handle 20 as indicated by the direction arrow 114. With the handle 20 pivotably coupled to the links 28 and the actuator 36 about the pivot axes 26 and 102, respectively, as discussed above, the pulling action of the handle 20 causes the plug 110 to uncover the tube 104, and the tip 46 of the actuator 36 moves up the gap 112 without abutting against the underside of the cover 14 such that there is no resistance by the cover 14 during the initial phase of pulling on the handle. With the tube 104 open to atmosphere, the vacuum pressure within the pocket 40 causes the outside air to enter the pocket 40 via the tube 104 to relieve the vacuum pressure therein. And as the handle 20 is pulled farther as indicated by the direction arrow 114, the leverage of the handle 20 assist the user to open the cover 14 as indicated by the direction arrow 116. That is, as the user continues to pull on the handle 20, the elongated slot 106 slides over the tube 104 and the tip 46 of the actuator 36 pushes upon the underside of the cover 14 to open the cover 14, without the vacuum pressure resistance, so that the cap 44 may unseal the pocket 40 to allow the user easy access to the medical devices and the medicine contained therein.

In order to hermetically seal another set of medical devices, the medical devices may be placed inside the pocket 40 and cover 14 may be closed. The handle 20 may be moved to the retracted position to seal the tube 104. Thereafter, vacuum pressure may be generated within the pocket 40 in a manner described above in reference to FIG. 3.

FIG. 6 shows a cross-sectional view of a sealable case system 120 for carrying a medical device. The case system 120 includes a case 10B configured to fluidly couple to a pump 122 to draw air out of the case 10B to hermetically seal the medical device within the case 10B. The case 10B may have similar features as the case 10, discussed above in reference to FIGS. 1-5, with the cover 14 having the cap 44 to enclose the pocket 40 formed within the outer sidewall 80 defining the housing 12. In this embodiment, the pocket 40 may be sized to hold one medical device 50A or 50B to minimize the size of the case 10B. Moreover, the first one-way valve 82 may be coupled to the sidewall 80 to draw air out of the pocket 40 as indicated by the direction arrow 84 but not in the opposite direction or into the pocket 40. Accordingly, once the cap 44 substantially seals the pocket 40, the air inside the pocket 40 may in effect be removed via the first one-way valve 82 to hermetically seal the item stored within the pocket 40.

The pump 122 may include a barrel 124 with a protruding tubular member 126 adapted to releasably couple to the first one-way valve 82. The barrel 124 may have a chamber 60 adapted to receive the plunger 68 having a first end 70 and a second end 72. The first end 70 of the plunger 68 may have one or more seals 74 to provide substantial air tightness between the plunger 68 and the chamber 60 as the plunger 68 moves in and out of the chamber 60 as indicated by the double ended direction arrows 76. The second end 72 of the plunger 68 may have an opening 78 to allow a user to grab onto the plunger 68 to move the plunger 68 in and out of the chamber 60. The tubular member 126 may have the second one-way valve 86 to draw air out of the chamber 60 as indicated by the direction arrow 88. Accordingly, once the cap 44 substantially seals the pocket 40 and the protruding tube element 126 is coupled to the first one-way valve 82, the air inside the pocket 40 may be removed via the first one-way valve 82. That is, as the plunger 68 moves from the retracted position, as shown in FIG. 6, to an extended position, the vacuum pressure may be created within the chamber 60 since the atmospheric air cannot enter the first chamber 60 due to the second one-way valve 86 that prevents atmospheric air from entering the chamber 60. The greater vacuum pressure within the chamber 60 relative to the pressure within the pocket 40 causes the air within the pocket 40 to flow from the pocket 40 through the first one-way valve 82, the tubular element 126, and into the first chamber 60, thereby creating a vacuum pressure within the pocket 40.

To generate additional vacuum pressure within the pocket 40, the plunger 68 may be reinserted into the chamber 60, which causes the air within the chamber 60 to exit via the second one-way valve 86 but not via the first one-way valve 82 to maintain the vacuum pressure generated within the pocket 40 due to the first cycle of withdrawing of the plunger 68. As the plunger 60 is cycled in and out of the chamber 60, in the manner discussed above, the vacuum pressure within the pocket 40 may be increased to hermetically seal the medical device and medicine stored within the pocket 40 to substantially isolate the items from the atmosphere. To open the cover 14 relative to the housing 12, the case 10B may include the handle and actuator system disclosed above in reference to FIGS. 4 and 5 in order to relieve the vacuum pressure within the pocket 40 before opening the cover 14. Once the vacuum pressure has been generated within the pocket 40, the pump 122 may be removed from the case 10B, and the user may conveniently carry the case 10B where its outer housing 12 may not be much bigger than the outer casing provided by the manufactures of the medical devices such as for EpiPen®.

FIG. 7 shows a cross-sectional view of another embodiment of a case 10C for carrying a medical device. The case 10B may include the first one-way valve 82 configured to fluidly couple to the pump 122 as discussed above in reference FIG. 6 to draw air out of the pocket 40 within the case 10C to hermetically seal the medical device therewithin. The case 10C may have similar features as the case 10B, with the cover 14 having the cap 44 to enclose the pocket 40 formed within the case 10C. In this embodiment, the housing 12 may include an inner wall 130 and an outer wall 132 with a chamber 134 between the two walls 130 and 132. The chamber 134 may be substantially vacuum sealed to minimize thermal conduction and/or convection to insulate the pocket 40 from extreme outer temperature fluctuations. In addition, the first one-way valve 82 may extend through the first and second sidewalls 130 and 132 to releaseably couple to the tubular element 126 of the pump 122 to generate vacuum pressure within the pocket 40 as discussed above. The pocket 40 may be sized to hold one or more medical devices 50A or 50B. The case 10C may also include the handle and actuator system disclosed above in reference to FIGS. 4 and 5 in order to relieve the vacuum pressure within the pocket 40 before opening the cover 14. While incorporating the vacuum chamber 134 may increase the overall size of the case 10C compared to the case 10B described above, the combination of vacuum pressure within the pocket 40 that is further insulated by the vacuum chamber 134 may substantially insulate the medical device within the pocket 40 from extreme temperature fluctuations to protect the medicine stored within the pocket 40.

Figure 8:
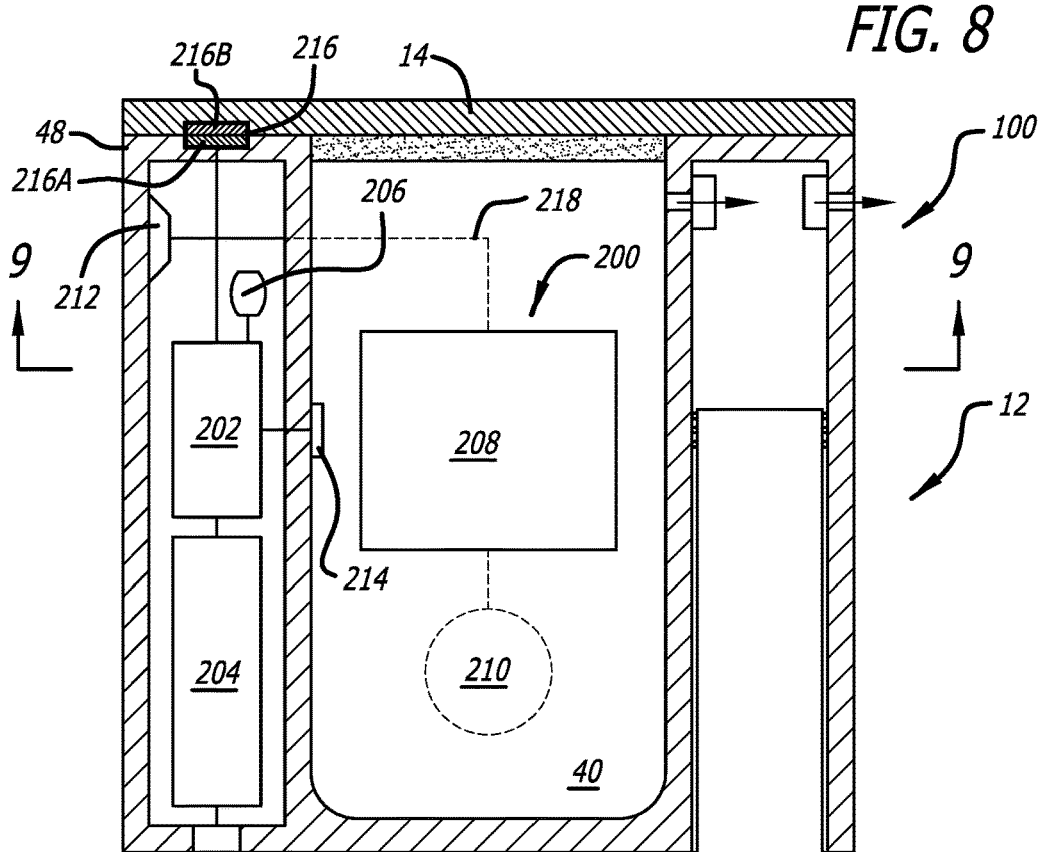
FIG. 8 shows the case incorporating a temperature adjustment system.

FIG. 8 shows the case 10D incorporating a temperature adjustment system 200 to monitor and adjust the temperature within the pocket 40 within a predetermined temperature range. The system 200 may include a processor 202 linked to a battery 204, a memory 206, a TEC 208, a fan 210, a communication device 212, a temperature sensor 214, and a detection sensor 216. The system 200 may also include a charger 220 with a plug 222 to connect to an electrical socket and a plug 224 to provide DC power to the battery 204 to charge the battery 204. This allows the case 10D to be used at home or be portable to be carried with the user depending on the application. Moreover, the pocket 40 may be provided with vacuum pressure, as discussed above in reference to FIG. 4, such that the pocket 40 may be more thermally insulated or isolated from the heat generated by the battery 204 within the second chamber 62 to minimize the temperature fluctuations in the pocket 40 due to the heat from the battery 204.

The processor 202 may control the battery 204 to provide power to the TEC 208 to control the temperature within the pocket 40. By way of background, the TEC 208 may utilize the Peltier effect where whenever direct current passes through the circuit of heterogeneous conductors, heat is either released or absorbed at the conductors' junctions, which depends on the polarity of direct current provided to the TEC. The amount of heat may be proportional to the current that passes through conductors. When direct current moves across a Peltier device, it causes temperature differential between the opposing sides. As a result, one side may be hotter compared to its opposite side or cooler than its opposite side, and vice versa, if the polarity of direct current is reversed. In general, if the heat generated on the hot side is effectively dissipated into heat sinks, such as a radiator, into the surrounding environment, then the temperature on the cold side may be much lower than that of the ambient by dozens of degrees. The TEC's cooling capacity may be proportional to the current passing through the interconnected conductors' junction layer.

Figure 9:
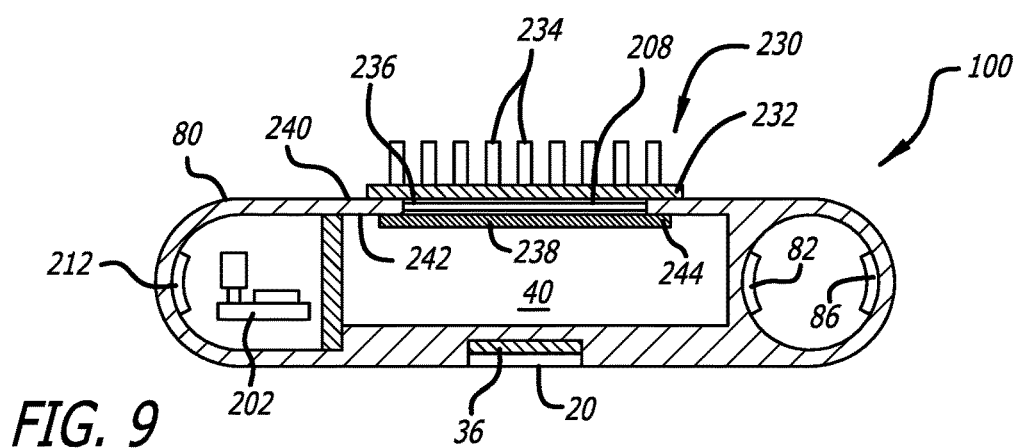
FIG. 9 shows a cross-sectional view of the case of FIG. 8 along the sectional-line 9-9.

FIG. 9 shows a cross-sectional view of the case 10D of FIG. 8 along the sectional-line 9-9 to illustrate that the TEC 208 may be placed within the sidewall 80 of the housing 12, and the TEC 208 may be located between a radiator 230 and a thermal plate 242. The radiator 230 has a base 232 with a plurality of fins 234 protruding therefrom. The TEC 208 has a first side 236 and a second side 238. The first side 236 may be thermally coupled to the base 232 of the radiator 220 to assist in dissipating heat or cold away from the first side 236, and the second side 238 of the TEC 208 may be thermally coupled to the thermal plate 242. Moreover, the first and second sides 236 and 238 of the TEC may be flush with the outer side 240 and inner side 242 of the sidewall 80, respectively, defining the pocket 40. The radiator 230 may be formed from a thermally conductive material such as aluminum or copper. The base 232 of the radiator may be sealed to the sidewall 80 to substantially prevent air from entering or existing the pocket 40. Direct current may be provided to the TEC 208 to cool or heat the thermal plate 238 thereby cooling or heating the pocket 40 in order to maintain the temperature inside the pocket within a desired or predetermined temperature range.

Figure 10:
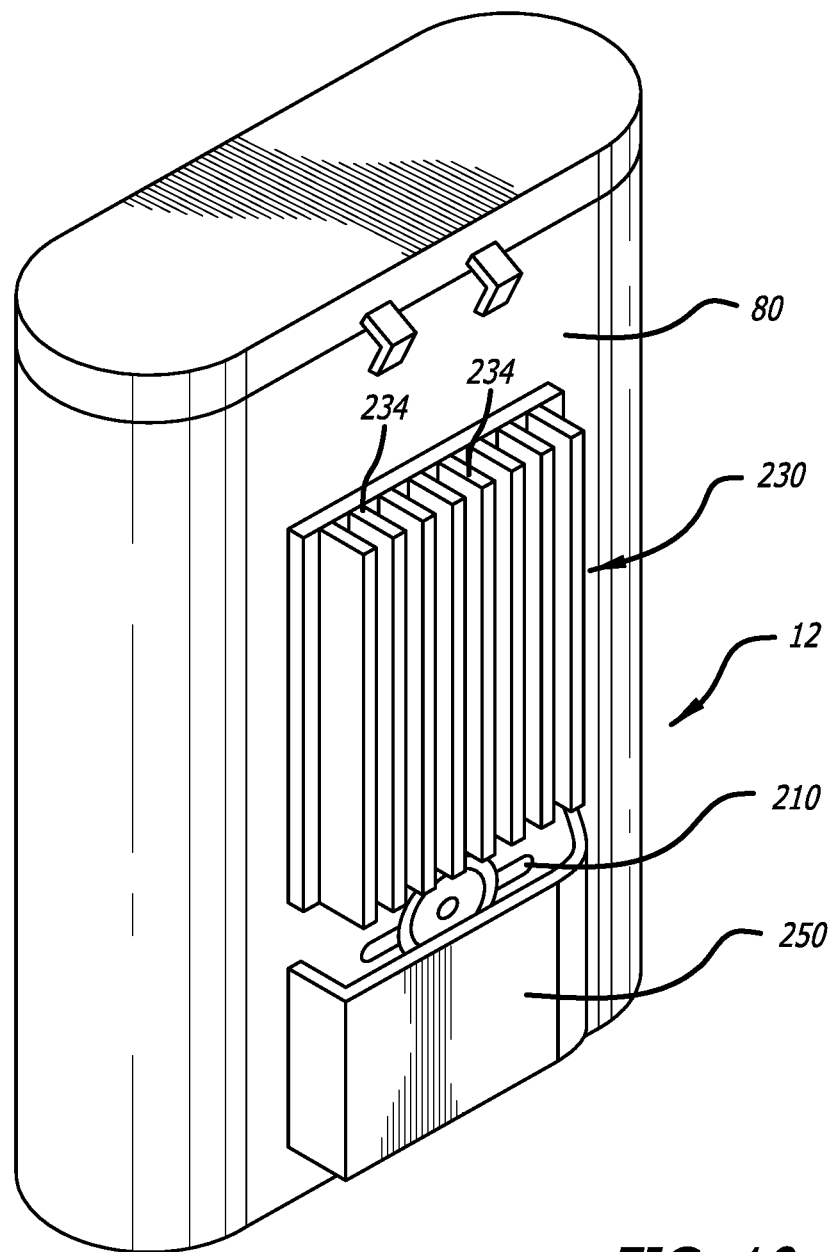
FIG. 10 shows a rear perspective view of the case illustrating a radiator coupled to the rear sidewall of the housing.

FIG. 10 shows a rear perspective view of the case 10D illustrating the radiator 230 coupled to the rear sidewall 80 of the housing 12, and the fan 210 covered by a vent 250. The vent 250 may direct the air blown by the fan 210 toward the fins 234 of the radiator 230 to dissipate heat away from the first side 236 of the TEC 208 into the atmosphere to further improve the performance of the TEC 208 and minimize the temperature variation between the first and second sides 236 and 238 of the TEC 208. Accordingly, with the combination of generating vacuum pressure within the pocket 40 to substantially thermally insulate the pocket 40 and being able to control cooling and/or heating the pocket 40 with the TEC 208, the temperature within the pocket 40 may be substantially maintained within a desired temperature range despite the extreme atmospheric temperature fluctuations thereby prolonging the potency and the life expectancy of the drug, such as epinephrine, stored within the pocket 40. Note that it is within the scope of the invention to utilize the TEC in a manner described above within the housing 12 that has the vacuum chamber 134 as discussed above in reference to FIG. 7.

A number of factors may impact the insulation of the medical device within the pocket 40 such as the amount of vacuum pressure generated by the user from cycling the plunger 68, time the case is exposed to the outer atmosphere, effectiveness of the seal around the cap 44, moisture in the air, the elevation or the altitude where the case is used, atmospheric temperature, and etc. In general, the vacuum pressure generated by manually cycling the plunger 68 within the chamber 60 may insulate the medical device from about 10° to about 30° F. for an average of about 20° F. below relative to the outside temperature for about 2 to 3 hours. For example, if a single insulated case such as the cases 10A and 10B, as described above, is carried outside with the initial temperature inside the pocket of about 80° F. (26.7° C.), and the outside the temperature is about 110° F. (43.3° C.), then the temperature inside the pocket 40 may rise to about 90° F. (32.2° C.) after about 2 to 3 hours of being exposed to the outside atmosphere. The performance of the double insulated case such as the case 10C described above may improve the insulation of the pocket 40 such that the temperature inside the pocket 40 may rise to about 90° F. (32.2° C.) after about 4 to 6 hours, for example, thus extending the period of insulating the pocket 40 compared to the single insulated case under similar atmospheric conditions. For many parts of the United States, and around the world, outside temperatures reaching above 110° F. (43.3° C.) is not uncommon during summer, such as in Phoenix, Ariz., and especially inside automobiles where the temperature can reach well over 140° F. (60.0° C.).

As with insulating the pocket 40, a number of factors may impact the performance of the TEC to cool or heat the pocket 40 such as the quality of the TEC, outside temperature, conductive material used for the radiator and thermal plate, thermal paste used to thermally couple the TEC to the radiator and the thermal plate, power of the fan, and etc. In general, the TEC may cool the pocket 40 from about 10° to about 30° F. for an average of about 20° F. below relative to the outside temperature. On the other hand, the TEC may heat the pocket 40 from about 30° to about 50° F. for an average of about 40° F. above relative to the outside temperature. For example, if the temperature inside the pocket reaches about 90° F. (32.2° C.), then the temperature adjustment system 200 may cool the pocket to about 70° F. (21.1° C.). As another example, if the pocket temperature reaches about 40° F. (4.4° C.), then the temperature adjustment system 200 may heat the pocket to about 70° to about 90° F. (21.1° C.-32.2° C.). Accordingly, the case may utilize single or double insulations, as discussed above, along with the temperature adjustment system 200 to substantially insulate the medical device stored in the pocket within a desired temperature rang such as from 59° to 86° F. (15°-30° C.), and a narrower preferred temperature range from 68° to 77° F. (20°-25° C.) to prolong the life expectancy of the medicine and its effectiveness such as epinephrine.

Figure 11:
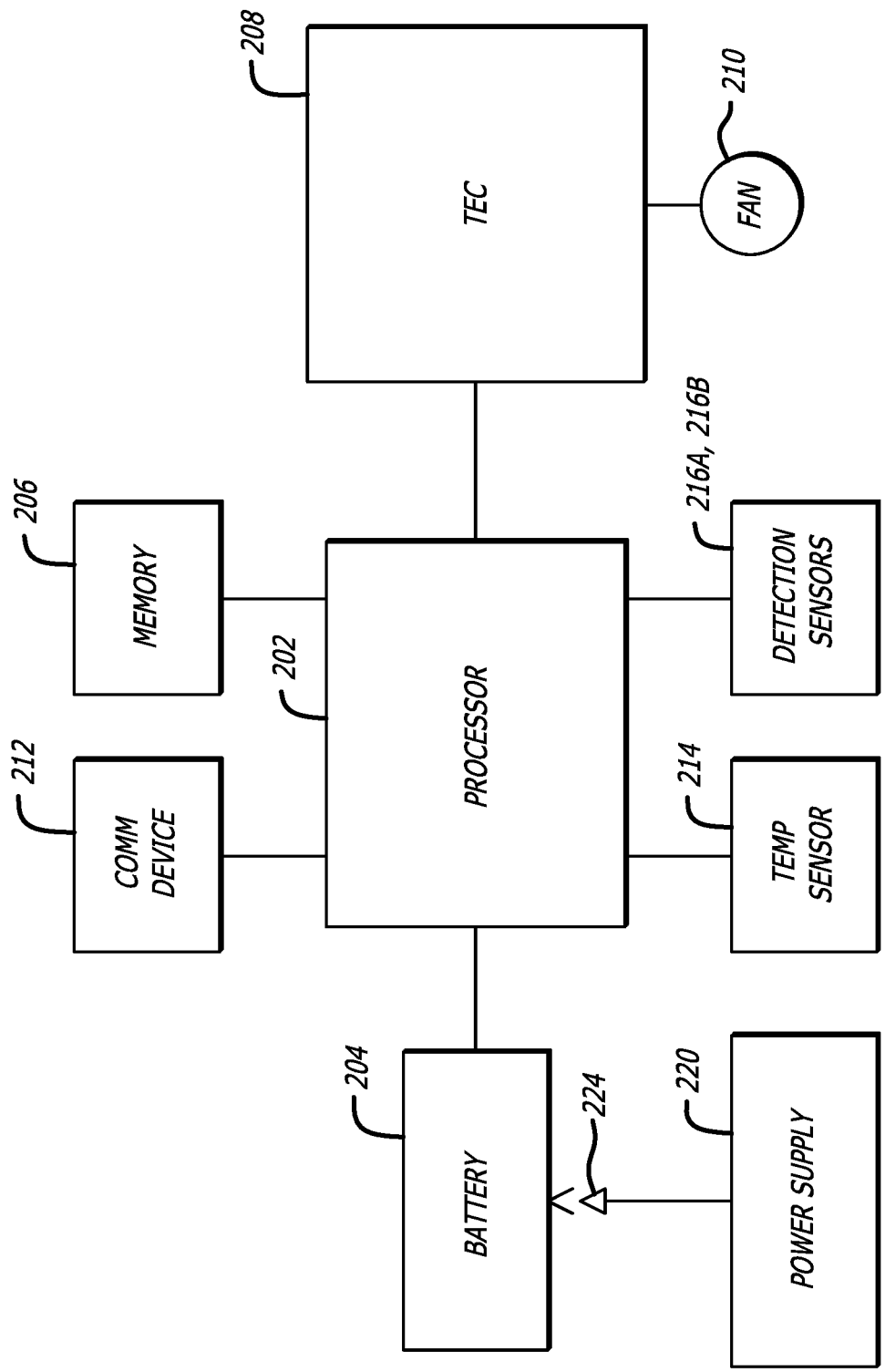
FIG. 11 shows an exemplarily electrical block diagram directed to the temperature adjustment system.

FIG. 11 shows an exemplarily electrical block diagram 260 representing the temperature adjustment system 200 to monitor and control the temperature within the pocket 40 within a predetermined temperature range. The diagram 260 may include the processor 202 communicably linked to the memory 206, the communication device 212, the temperature sensor 214, and the detection sensor 216. The processor 202 may be electrically coupled to the battery 204, the TEC 208, and the fan 210 to allow the processor 202 to provide the direct current from the battery 204 to the TEC 208 and the fan 210 based on the information provided by the temperature sensor 214 when compared to the predetermined parameters stored in the memory 206. In addition, the diagram 260 may also include the charger or power supply 220 with a plug 224, which may be releasably connected to the battery 204 so that the plug 224 may be disconnected to allow the user to carry the case 10D when traveling or used at home depending on the application. Alternatively, the block diagram 260 may also include a power vacuum pump that can be controlled by the processor 202 to turn on the pump in case the vacuum pressure within the pocket falls below the desired vacuum pressure setting stored in the memory 206.

Figure 12:
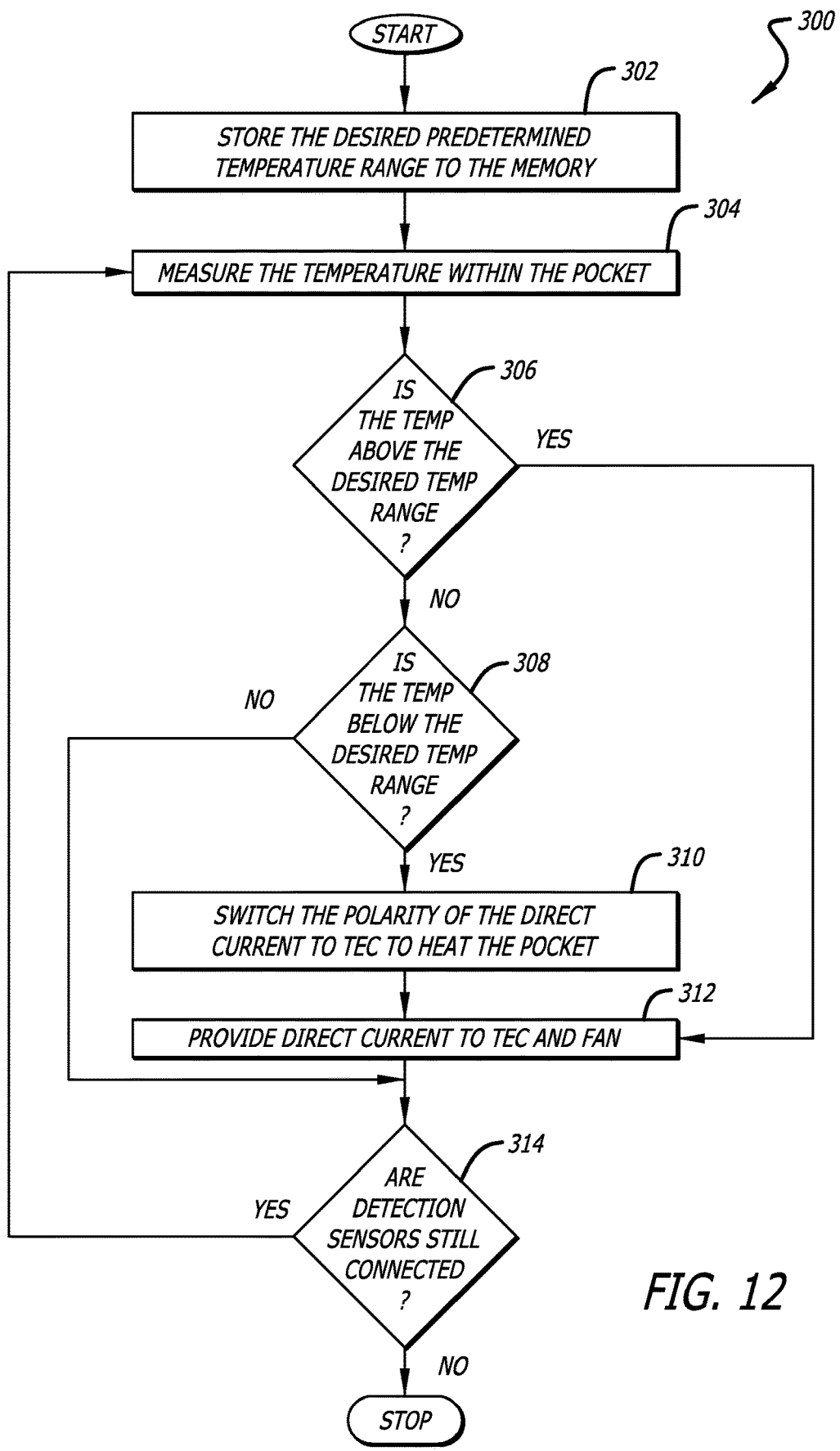
FIG. 12 shows a flow chart illustrating the method of controlling the temperature within the pocket in reference to the electrical block diagram in reference to FIG. 11.

FIG. 12 shows a flow chart 300 illustrating a method of controlling the temperature within the pocket 40 in reference to the electrical block diagram 260 in reference to FIG. 11 disclosed above. In step 302, the desired temperature range of the pocket 40 may be stored into the memory 206. For instance, to maintain the potency and to prolong the lifespan of the drug epinephrine contained within the medical devices 50A and 50B, the memory 206 may be stored with data to keep the temperature of the pocket 40 between 59°-86° F. (15°-30° C.) as a first predetermined temperature, and alternatively a narrower temperature range of 68°-77° F. (20°-25° C.) as a second predetermined temperature. In step 304, the temperature sensor 214 may measure the temperature within the pocket 40. In step 306, the processor 202 may be linked to the temperature sensor 214 to monitor the temperature of the pocket 40, and compare the measured temperature with the predetermined temperature range stored in the memory 206. If the measured temperature is above the upper desired temperature range, then the processor 202 may provide power from the battery 204 to the TEC 208 and the fan 210 as noted in step 312. The power to the TEC 208 may cool the second side 238 to lower the temperature within the pocket 40, and the fan 210 may blow air through the fins 234 to cool the hotter first side 236 of the TEC. In step 308, if the measured temperature is not above the desired temperature range, then a comparison may be made to determine if the measured temperature is below the desired temperature range stored in the memory 206. If so, then in step 310, the polarity of the direct current provided to the TEC 208 may be reversed so that the second side 238 may be hotter than the first side 236 of the TEC 208 in order to raise the temperature within the pocket 40. In step 312, the power to the fan may be provided and direct current with reverse polarity may be provided to the TEC 208 to raise the temperature within the pocket 40. In step 314, the processor may determine if the detection sensors 216A and 216B embedded within the top side 48 of the housing 12 and the cover 14, respectively, are still connected, which indicates that the cover 14 is in a closed position thereby sealing the pocket 40. If so, the processor 202 returns to the step 304 to measure the temperature within the pocket. On the other hand, if the detection sensors 216A and 216B are separated, then this may indicate that the cover 14 is in an open position so that the processor 202 may stop monitoring the temperature within the pocket 40. Moreover, if the detection sensors 216A and 216B are separated, then the processor may send an urgent signal through the communication device 212 to the user's mobile device to send out a request for emergency assistance.

Figure 13:
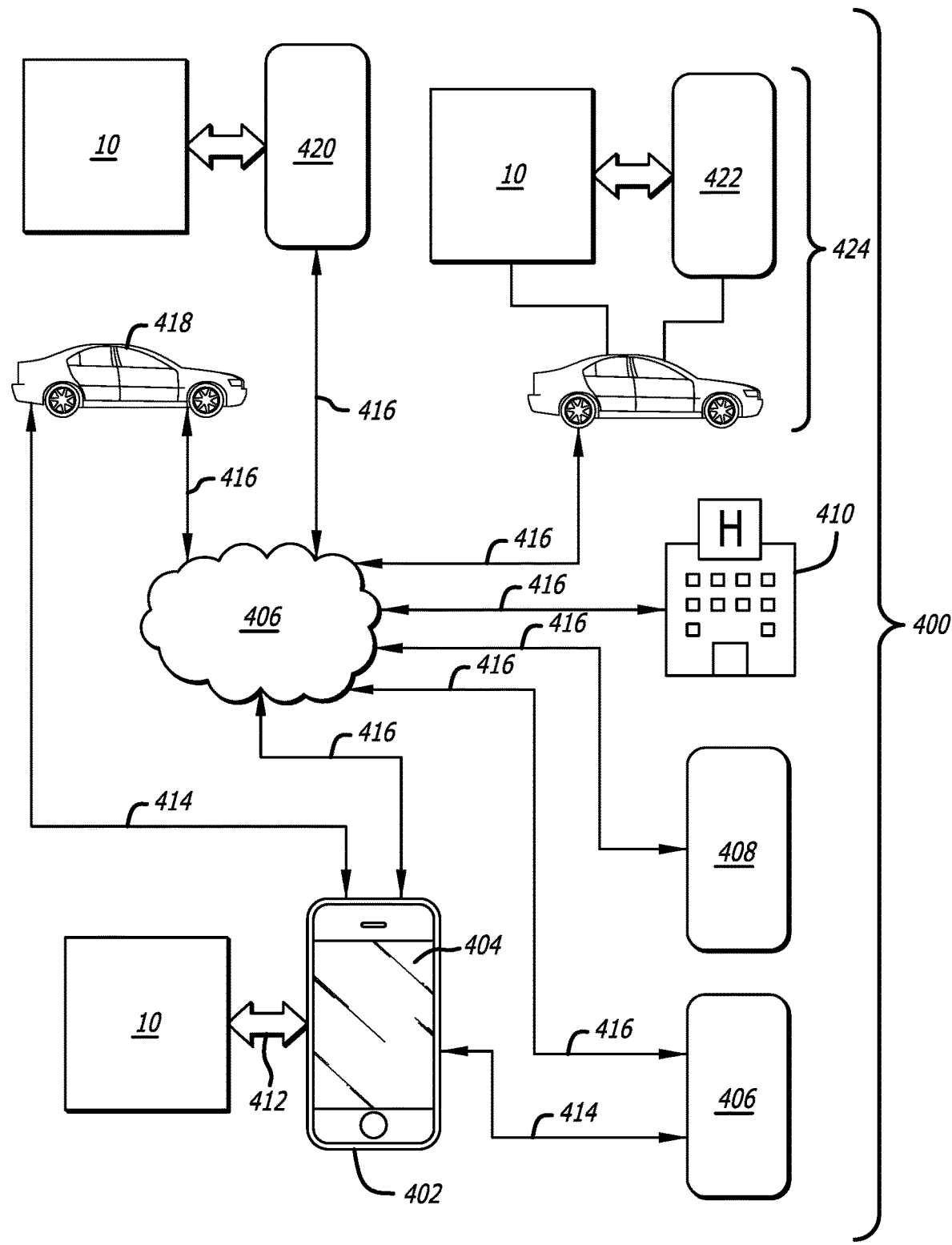
FIG. 13 illustrates an urgent care system to provide an efficient delivery of the necessary drug(s).

FIG. 13 illustrates an urgent care system 400 to provide an efficient delivery of the necessary drug(s), such as epinephrine and/or any other necessary drugs, to a person who is in need of urgent medical care. The system 400 may include user's mobile phone 402 communicably connected to the case 10D containing one or more of the medical devices 50 as described above. The mobile phone 402 may connect to the case 10D wirelessly and/or hard wire. In this regard, the mobile phone 402 may connect to the processor 202 via the communication device 212, shown in FIG. 11, to perform a variety of functions as discussed in more detail below. As discussed above, the case 10D may be portable so that the user can carry the case 10D along with the phone 402 as the user travels such that the phone 402 and the case 10D may remain connected. The phone 402 may download an application software 404 from a network 406 such as the Internet, cloud, application website and/or cellular tower. The application software 404 may request and store a variety of information about the user such as emergency contact information of the parents, hospital, doctor, and etc. For instance, the application software 404 may include the phone numbers of the parents or next to kin 406, the doctor's phone number 408, and hospital 410 or the like to contact automatically in case of an emergency.

In reference to FIGS. 8 and 11, if the processor 202 detects that the detection sensors 216A and 216B are disconnected, then this may indicate that the user has opened the cover 14 of the case 10D in order to use the medical devices 50; thus, indicating an emergency situation requiring an immediate response. Under such circumstances, the processor 202 may send an emergency signal 412 via the communication device 212 to the user's phone 402. Once the signal 412 is received, the software 404 may activate a protocol such as to call or send an emergency text messages to the emergency contacts such as the parents or next to kin 406, the doctor's phone number 408, and hospital 410 to notify of them of the urgent situation. For priority contacts such as parents or next to kin, the user's phone 402 may communicate through a direct communication line 414 such as through the mobile network; and for secondary emergency contacts such as to doctors 408 and hospital and/or ambulance 410, the phone 402 may communicate through the network 406 via the secondary communication lines 416, which may also include the priority contacts 406 to ensure they get the notification.

The application software 404 may also be preprogrammed to automatically contact a mobile transportation or ride-sharing service 418 such as UBER®, LYFT® and/or ambulance with a priority service with the pickup location based on the location of the phone 402 and the address of the hospital 410 based on the information stored in the phone 402 to transport the user to an emergency treatment center 410 without having the user drive his or her own vehicle when the user may not be in a proper physical condition to drive the vehicle or for minors who cannot drive. The phone 402 may contact the mobile transportation service 418 via a direct communication line 414 and/or indirect communication line 416.

The system 400 may also connect other users of the case 10D to the user 402 via the network 406 for assistance. For instance, if the user 402 is without the case 10D or the medical device during an allergic reaction, the application software 404 may have a backup notification which the user can activate to seek assistance from other users nearby who has a medical device. That is, the system 400 may include a second type of users 420 and a third type of users 422. The second type of users may be people who carry a medical device with them, and the third type of users 422 may be mobile transportation drivers such as drivers for UBER® and LYFT®. For example, in situations where the user 402 is without the case 10D or if the medical device has expired or if the user needs another shot of the drug from the medical device, the user 402 may activate the backup notification such that the phone 402 sends the notification to the network 406 via the communication line 416. The network 406 may then search the data base for other users nearby the user 402 based on the locations of the other users' phones 420 and 422, and request for assistance. For instance, mobile transportation drivers 422 may carry a case 10D or medical devices 50 with them in their vehicles 424, and when driver receives a notification for an emergency assistance, the driver nearby or nearest the user 402 may accept the notification and drive to the user 402 and deliver the case 10D and/or the medial device to be administered and drive the user to an emergency facility 410 for further treatment. Alternatively, the user 402 may receive a request for assistance from the other users such as the user 420, and if the user 402 is in a position to assist the user 420, the user 402 may accept the request and allow the other user 420 to use the user's 402 medical device 10.

The network 406 may also collect information from all the cases 10D utilized within the system 400 and provide helpful analytics information to the users. For instance, the case 10D may communicate the temperature within the pocket 40 to the phone 402 via the communication device 212 and the application software 404 may forward the temperature information to the network 406 to keep a record the temperature fluctuations within the pocket 40. The network 406 may periodically request the user to check the medical device 50 to determine if the drug is still potent such as by inspecting if the epinephrine is still clear—which may be an indication that the drug is still potent and effective. If the epinephrine is not clear, this may be an indication that the drug is no longer potent. Such information about the temperature exposure history of the medical devices, the period of time it took for the drug to lose its potency, the geographic location of the drug, climate, and the like may be gather from the users within the system 400 and analyzed to predict a more accurate lifespan and effectiveness of the drug. Based on such analytics, the network 406 may send a notification to the application software 404 with its best predictions on the effectiveness of the drug along with recommendation on how to store the drug and when to replace the drug or medical device.

Figure 14:
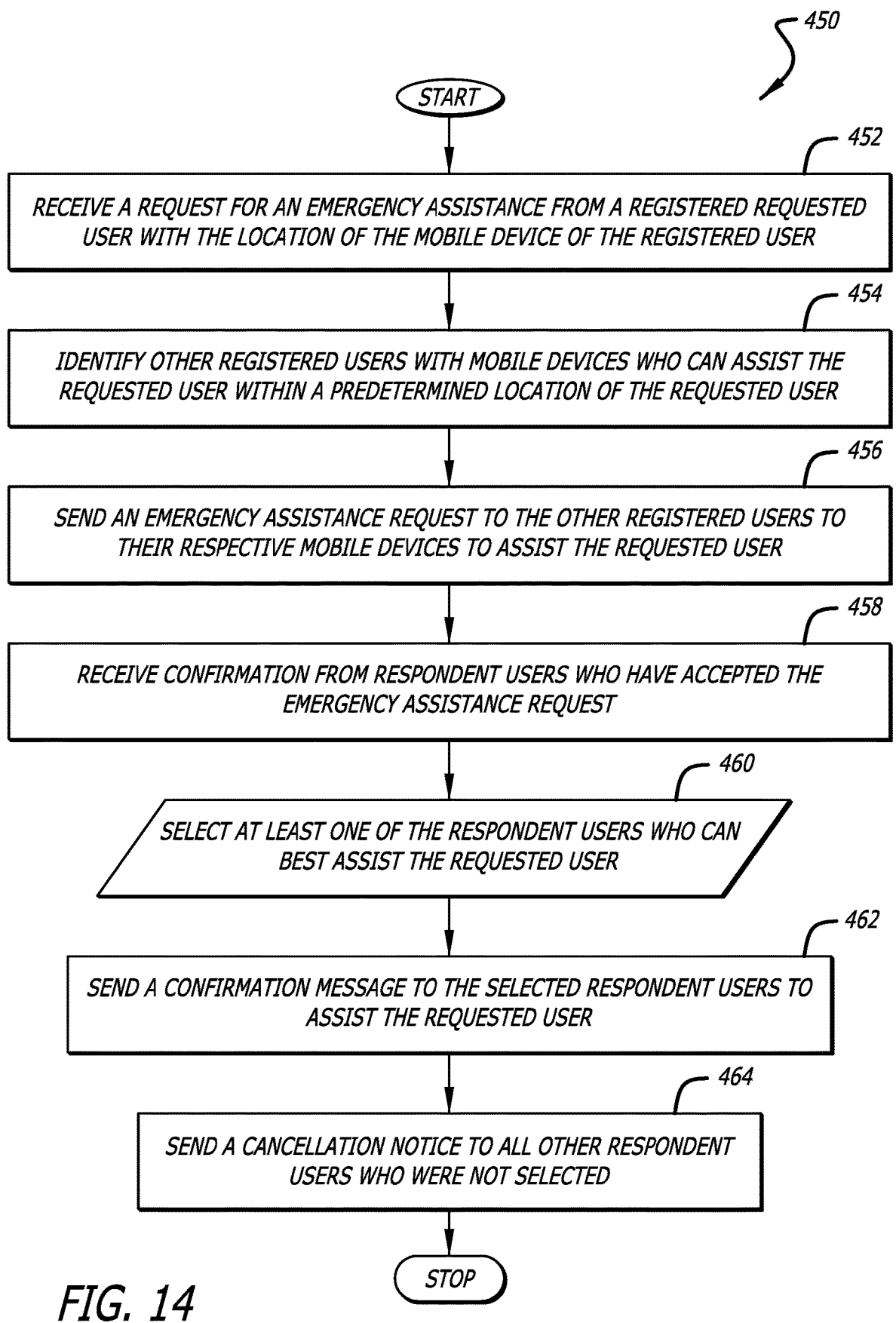
FIG. 14 shows a flow chart illustrating a method of assisting a user in need of a medical device.

FIG. 14 shows a flow chart 450 illustrating a method of assisting a user in need of another medical device 50. In step 452, the network 406 may receive a request for an emergency assistance from a registered user via the user's mobile device with the location of the mobile device and the nature of the emergency. In step 454, the network 406 may identify other registered users within the network with mobile devices with medicine within a predetermined range of the requested user who can assist the requested user based on their proximity to the requested user and the nature of the emergency. In step 456, the network 454 may send an emergency assistance request to other registered users who have been identified in step 454. In step 458, the network 406 may receive confirmation from respondent users who have accepted the emergency assistance request. For instance, if the requested user attends the same school or work within the same office building as the potential respondent user, then the potential respondent users may be a good candidate to accept the confirmation to assist the requested user. In step 460, the network may select at least one of the respondent users who can best assist requested user. For instance, if the respondent user has the proper medicine that is effective and nearest to the requested user. In step 462, the network 406 may send a confirmation message to at least one of the respondent users selected from the selecting step 460 to assist the user of the requested user. In step 464, the network may send a cancellation notice to all other respondent users who were not selected from the selecting step 460. Accordingly, even if one of the users within the network 406 forgot to take the case 10D with them during their travels, or if the medicine is no longer effective, or if the user needs another shot of the medicine, then the user can utilizes the network as a backup to such emergency medical needs. In particular, if the respondent user is a mobile vehicle 424, then the mobile vehicle can assist with administering the medicine and transport the user to a medical clinic for the necessary medical treatment. Such a network of users may minimize the need for users to have multiple medical devices in locations where they frequently reside such as home, office, school, and cars, thereby reducing the cost associated with the medical devices, especially as the medical devices may expire yearly.

While various embodiments of the invention have been described, it will be apparent to those of ordinary skill in the art that many more embodiments and implementations are possible within the scope of this invention. Moreover, various features and functionalities described in this application and Figures may be combined individually and/or plurality of features and functionalities with others. Accordingly, the invention is not to be restricted except in light of the attached claims and their equivalents.

What is claimed is:

1. A case for storing medicine, the case comprising:
a housing having an outer sidewall with an inner wall dividing a pocket and a chamber, the pocket adapted to receive a medical device;
a cover adapted to open and close to seal the pocket;
a first one-way valve coupled to the inner wall to allow air to pass from the pocket to the chamber;
a plunger adapted to move within the chamber between an retracted position and an extended position such that as the plunger moves from the retracted position to the extended position air within the pocket flows through the first one-way valve and into the chamber to generate a vacuum pressure within the pocket that is lower than the atmospheric pressure; and
a handle and an actuator, the handle having a first end and a second end, the actuator having a base end and a tip end and adapted to slide along the outer sidewall of the housing, the first end of the handle pivotably coupled to the base end of the actuator such that when the handle is in a retracted position the tip end is positioned adjacent to the cover, and when the second end of the handle is in an extended position the tip end pushes up the cover to move the cover into an open position.

2. The case according to claim 1, wherein the outer sidewall has a passage opening to provide an air passage to the pocket when the passage opening is open to the atmosphere, the handle having a plug that closes the passage opening when the handle is in the retracted position and a gap is formed between the tip end and the cover, and as the handle moves from the retracted position to the extended position, the plug opens the passage opening to relive the vacuum pressure within the pocket and the tip end extends across the gap before pushing up the cover to the open position.

3. The case according to claim 1, further including a second one-way valve coupled to the outer sidewall to allow air to pass from the chamber to the atmosphere such that as the plunger moves from the extended position to the retracted position, the air within the chamber flows through the second one-way valve but not the first one-way valve.

4. The case according to claim 1, further including a thermoelectric cooler (TEC) juxtaposed to the pocket such that powering the TEC can either cool or heat the pocket.

5. The case according to claim 4, further including a temperature sensor that monitors the temperature within the pocket and a processor that controls the power provided to the TEC to cool the pocket if the measured temperature is above the desired temperature range and heat the pocket if the measured temperature is below the desired temperature range.

6. The case according to claim 5, further including a battery communicably coupled to the processor to control the battery to deliver power to the TEC to either cool or heat the pocket.

7. The case according to claim 5, further including first and second detection sensors and a communication device, the first detection sensor coupled to the cover and the second detection sensor coupled to the housing such that when the cover is closed relative to the housing, the first and second detection sensors are closed and when the cover is open relative to the housing, the first and second detection sensors are open, the communication device communicably coupled to the processor and capable of wirelessly communicating with a mobile phone such that when the first and second detection sensors detect that the cover is open relative to the housing, the processor sends a message to the mobile phone that the cover is open.

* * * * *